United States Patent [19]

Hoang et al.

[11] Patent Number: 5,334,388
[45] Date of Patent: Aug. 2, 1994

[54] ANTIMICROBIAL DRYING SUBSTRATE

[75] Inventors: Minh Q. Hoang, Taylorsville; Mohammed A. Khan, Sandy, both of Utah

[73] Assignee: Becton, Dickinson and Company, Franklin Lakes, N.J.

[21] Appl. No.: 122,829

[22] Filed: Sep. 15, 1993

[51] Int. Cl.$^5$ .................................. A01N 25/34
[52] U.S. Cl. ............................ 424/402; 424/404; 424/405; 424/414; 252/106; 252/DIG. 5
[58] Field of Search ........... 424/402, 404, 405, 414 C; 422/25 C; 252/106 C, DIG. 5 C

[56] References Cited

U.S. PATENT DOCUMENTS

| | | | |
|---|---|---|---|
| 4,134,412 | 1/1979 | Gross et al. | 132/7 |
| 4,202,881 | 5/1980 | Gross et al. | 424/70 |
| 4,257,907 | 3/1981 | Langguth et al. | 252/106 |
| 4,319,956 | 3/1982 | Snyder et al. | 162/146 |
| 4,326,977 | 4/1982 | Schmolka et al. | 252/106 |
| 4,456,543 | 6/1984 | Owens | 252/106 |
| 4,690,821 | 9/1987 | Smith et al. | 424/401 |
| 4,804,750 | 2/1989 | Nishimura et al. | 536/20 |
| 4,882,221 | 11/1989 | Bogart et al. | 428/308.8 |
| 4,883,475 | 11/1989 | Bogart et al. | 604/290 |

FOREIGN PATENT DOCUMENTS

72440/87  5/1986  Australia ................ A47L 13/17

*Primary Examiner*—Thurman K. Page
*Assistant Examiner*—Jyothsna Venkat
*Attorney, Agent, or Firm*—Nanette S. Thomas

[57] ABSTRACT

A dry towel or wipe comprising an absorbent paper substrate which is uniformly coated and dried with an antimicrobial formulation comprising a volatile liquid, an active antimicrobial agent, a water soluble polymer, a polyalkylene glycol an emollient and water. The treated towel is useful in providing antimicrobial effectiveness for drying skin in preparation for surgical procedures without irritating or drying the skin.

2 Claims, No Drawings

ANTIMICROBIAL DRYING SUBSTRATE

BACKGROUND OF THE INVENTION

1. Field of the Invention

This invention relates to a dry substrate for drying hands after scrubbing or drying skin after patient pre-operation prepping without irritating or drying the skin. The dry substrate comprises a towel or a wipe coated with an antimicrobial formulation.

2. Description of Related Art

Effective antiseptic or disinfectant dry wipes can be formed by combining an antimicrobial formulation with a suitable carrier. Thus, antiseptic compounds can be formulated rather easily, however, many such dry wipes are not suitable for use in contact with human skin due to the abrasive nature of the surfactant-containing composition.

Where the dry wipe is intended for use as for drying during surgical scrub procedures, mildness is an important consideration. Mildness indicates the dry wipe does not cause excessive irritation of the skin, such as erythema.

Surgical scrub procedures and techniques are highly conducive to the development of erythema and other irritations. All personnel involved in surgical procedures use a surgical scrub in preparation for surgery. Frequently, the same individual will scrub three to five times on a single day. A typical surgical scrub involves placing a cleansing composition on the hand. Commonly, a brush or sponge is used and the arms from the elbows to the fingertips are scrubbed thoroughly for as long as ten minutes. Thus, the epidermal layers of the skin are subject to significant rubbing and aggravation. After the arms and hands have been scrubbed, they are rinsed, dried and placed into rubber gloves. Since the rinse is often not complete and residual surfactant and/or antimicrobial compounds from the cleansing composition are left on the skin, further irritation may be experienced when they are dried with a towel or wipe. This in turn can create topical skin irritations.

The likelihood of irritation or erythema increases with the frequency one performs the surgical scrub procedure. Therefore, it is not only important that the surgical scrub composition be very mild, but that the dry wipe be mild as well.

Therefore, there exists a need for a dry wipe which provides substantially maximized efficacy and does not promote dryness or irritation to the skin.

SUMMARY OF THE INVENTION

The present invention is a dry towel or wipe comprising an absorbent paper substrate which is coated and dried with an antimicrobial formulation. The antimicrobial formulation desirably comprises a volatile liquid, an active antimicrobial agent, a water soluble polymer, polyalkylene glycol, a moisturizer and/or emollient, water and a buffer for adjusting the pH of the formulation.

Most preferably, the antimicrobial formulation composition comprises:

(a) from about 50% to about 75% of a volatile liquid;
(b) from about 0.05% to about 1.5% of an active antimicrobial agent;
(c) from about 0.01% to about 2.5% of a water soluble polymer;
(d) from about 0.5% to about 1.5% of a polyalkylene glycol;
(e) from about 0.5% to about 1.5% of moisturizer and/or emollient;
(f) from about 24% to about 27% of water; and
(g) a sufficient amount of a pH adjusting component to achieve a pH of about 4.5 to about 7.5.

Most preferably, the dry antimicrobial towel is prepared by dipping or spraying a towel or similar substrate with the antimicrobial formulation and then drying the towel.

A significant advantage of the dry antimicrobial towel of the present invention is its use in the healthcare profession as an effective means for drying hands after surgical scrub preparation or for drying skin after patient pre-operation and prepping while providing substantial antimicrobial effectiveness, as well as non-irritancy or drying to the skin. The dry antimicrobial towel of the present invention can also be used for wiping surgical table tops, instruments, or anything that requires wiping and drying.

A further advantage of the dry antimicrobial towel includes its use to clean and prep the patient's surgical site and its use under the patient or even over the patient to absorb any fluid runoffs without irritating the skin.

DETAILED DESCRIPTION

The present invention may be embodied in other specific forms and is not limited to any specific embodiments described in detail which are merely exemplary. Various other modifications will be apparent to and readily made by those skilled in the art without departing from the scope and spirit of the invention. The scope of the invention will be measured by the appended claims and their equivalents.

The dry antimicrobial towel of the present invention is most preferably prepared with the following antimicrobial formulation:

(a) a volatile liquid;
(b) an active antimicrobial agent;
(c) a chitosan or a high polymer amine;
(d) a polyalkylene glycol;
(e) a moisturizer and/or emollient;
(f) water; and
(g) a pH adjusting component.

The volatile liquid is such that it is compatible with the other ingredients in the formulation and the substrate to be coated and readily passes off by evaporation. Particularly useful are water and alcohols. Alcohols include ethyl alcohol and mixtures thereof.

An alcohol is preferably used in the antimicrobial formulation for applying the antimicrobial formulation to the towel. The alcohol evaporates from the formulation once it is applied to the towel.

An alcohol for use in the antimicrobial formulation includes, but is not limited to, alkanol and arylalkanol.

The preferred alcohols for use in the antimicrobial formulation is isopropanol or ethanol. Preferably, isopropanol may present in the antimicrobial formulation in an amount from about 65 to about 75 weight percent, and most preferably at about 70 weight percent. Alternatively, ethanol may be present in the antimicrobial formulation in an amount from about 50 to about 60 weight percent and most preferably at about 60 weight percent.

An antimicrobial agent is a compound or substance that kills microorganisms or prevents or inhibits their growth and reproduction.

The antimicrobial agent present in the antimicrobial formulation composition is selected so as not to upset desirable physical and chemical properties of human skin. A properly selected antimicrobial agent maintains stability under use and storage conditions (pH, temperature, light, etc.), for a required length of time. A desirable property of the antimicrobial agent is that it is safe and nontoxic in handing, formulation and use, is environmentally acceptable and cost effective.

Classes of antimicrobial agents include, but are not limited to, chlorophenols, biguanides, antibiotics and biologically active salts.

The preferable antimicrobial agent in the antimicrobial is chlorhexidine gluconate or parachlorometaxylenol (PCMX). Preferably, chlorhexidine gluconate is present in the antimicrobial formulation in an amount from about 0.5 to about 1.5 weight percent, and most preferably at about 1.0 weight percent. Alternatively, PCMX may be present in the antimicrobial composition in an amount from about 0.25 to about 1.0 weight percent and most preferably at about 0.5 weight percent.

A chitosan is a high polymer amine and adapted to form salts with acids. A chitosan is typically characterized as a water soluble polymer.

A preferred chitosan in the antimicrobial composition is a chitosonium pyrrolidone carboxylate, Kytamer® PC (trademark of Amerchol Corporation, Edison, N.J.) sold by Amerchol.

A chitosan is used in the antimicrobial formulation for leaving a film on the skin after wiping. The selection of the chitosan is based on its film forming, biocompatible and humectant properties.

Preferably, chitosan is present in the antimicrobial formulation in an mount from about 0.25 to about 0.75 weight percent, and most preferably at about 0.5 weight percent.

A polyalkylene glycol is used in the antimicrobial formulation for lubricating and conditioning of the skin. A polyalkylene glycol is a synthetic oily substance and is typically characterized as a skin conditioner. The selection of a polyalkylene glycol is based on its biocompatibility and its ability to protect the skin from drying and chapping.

A preferable polyalkylene glycol in the antimicrobial composition is a 14 butyl ether, UCON® Fluid AP (trademark of Amerchol Corporation, Edison, N.J.) sold be Amerchol.

Preferably, the polyalkylene glycol is present in the antimicrobial composition in an amount from about 0.5 to about 1.5 weight percent and most preferably at about 1.0 weight percent.

Emollients in their physical form are thin liquids, oils of various viscosities, fatty solids or waxes. Hydrocarbons function essentially as emollients by virtue of their ability to lubricate and/or hold water at the skin surface due to their relative occlusively. Mineral oil is such a fluid. Some emollients are hydrophilic (glycerin, propylene glycol) and are water soluble lubricants and humectants. Since emollients may be fatty chemicals, oily or waxy in nature, they can impart barrier properties to formulations and are then referred to as moisturizers.

Moisturizers are substances which provide external lubricant behavior, such as to soften and soothe the skin because they encourage skin water retention.

The function of the moisturizer and/or emollient in the antimicrobial formulation is to provide relief for dry and sensitive skin. Therefore, chapping of the skin may be prevented. In addition, the moisturizer and/or emollient does not leave a tacky after feel on the skin.

Suitable moisturizers and/or emollients in the antimicrobial formulation includes derivatives of lanolin such as the ethoxylated acetylated alcohol and surface active alcohol derivatives of lanolin, propylene glycol, polypropylene glycol, polyethylene glycol, lanolin and lanolin derivatives, mineral oils, fatty alcohols and glycerin.

A preferable moisturizer and/or emollient for the antimicrobial formulation is a polyethyl glycol lanolin derivative, PEG® 75 lanolin (trademark of Amerchol Corporation, Edison, N.J.) sold by Amerchol Corporation.

Another preferable moisturizer and/or emollient for the antimicrobial formulation is an ethoxylated (75 moles) lanolin, Solulan® L-575 (trademark of Amerchol Corporation, Edison, N.J.) sold by Amerchol Corporation.

Preferably, a moisturizer and/or emollient is present in the antimicrobial formulation in an amount from about 0.5 to about 1.5 weight percent and most preferably at about 1.0 weight percent.

Because the antimicrobial composition is greatly influenced by pH, small mounts, less than about 1.0 weight percent of a nontoxic acidic substance may be added so as to maintain an effective level.

Suitable nontoxic acidic substances include sodium hydroxide, hydrochloric acid, sulfuric acid, phosphoric acid, citric acid, lactic acid and gluconic acid.

The formulation may be adjusted to a pH within the range from about 4.5 to about 7.5 and most preferably at about 5.0. Adjustment of the pH is desirable so that the formulation is skin compatible.

The balance of the antimicrobial formulation is preferably water. The water may be present in the antimicrobial formulation in an amount from about 20 to about 50 weight percent.

Other ingredients which are conventional or desirable in various cosmetic formulations may also be added to the antimicrobial formulation as long as they do not adversely affect the overall properties of the antimicrobial formulation.

If desired, the antimicrobial formulation of the invention may include a perfume to provide a pleasing scent or a dye to provide a characteristic color.

The dry antimicrobial towel is prepared by uniformly applying the antimicrobial formulation to a towel and then allowing the treated towel to air dry, either at room temperature or elevated temperatures which are not detrimental to the substrate or ingredients incorporated therein. The formulation may be applied by any known processes such as immersion of the towel in the formulation, spraying the solution onto the towel or coating the towel by means of a suitable applicator.

The towel is most preferably paper and can be in any form convenient for wiping non-absorbent surfaces but is preferably in sheet-like form. It is derived from any paper stock which is produced by any of the well known manufacturing methods. The paper preferably has a wet strength sufficient to preclude disintegration of the wipe during use. Furthermore, although paper having a preferred wet strength will not disintegrate during use, nonetheless, it is sufficiently disintegratable to permit convenient disposal of a used towel by flushing down a toilet without harm to any part of a toilet system, i.e., a septic tank.

The paper towel is also capable of absorbing an amount of water sufficient to result in dissolution of a major amount of the active ingredients present in the wipe in order to facilitate transfer of effective amounts of the active ingredients from the wipe to the surface being cleansed and disinfected.

Suitable paper towels are disclosed in U.S. Pat. Nos. 4,690,821, 4,882,221, 4,883,475 and 4,319,956.

The following examples are not limited to any specific embodiment of the invention, but are only exemplary.

EXAMPLE 1

Preparation of Antimicrobial Formulation A And Application To A Paper Substrate

Antimicrobial formulation A was formed with the following ingredients:

| Ingredients | Weight Percent |
| --- | --- |
| Isopropanol | 70.0 |
| Chlorhexidine Gluconate (20% w/v) | 1.0 |
| Kytamer ® PC | 0.05 |
| PET ® 75 lanolin | 1.0 |
| U-Con ® fluid AP | 1.0 |
| Water | 26.94 |
| Fragrance 1626-Hr | 0.01 |
| Sodium Hydroxide (5N) | q.s. |
| Hydrochloric Acid (6N) | q.s. |

Kytamer ® was mixed with water until the solid was completely dissolved and a clear solution was obtained. Isopropanol, chlorhexidine gluconate, PEG ® 75 lanolin, U-Con ® fluid AP and the fragrance were then mixed into the clear solution. The pH of the solution was then adjusted to about 5.0±0.5 by the addition of sodium hydroxide and hydrochloric acid.

Paper substrates were then dipped into antimicrobial formulation A and dried.

EXAMPLE 2

Preparation of Antimicrobial Formulation B and Application To A Paper Substrate

Antimicrobial formulation B was formed with the following ingredients:

| Ingredients | Weight Percent |
| --- | --- |
| Ethanol | 60.0 |
| Parachlorometaxylenol | 0.50 |
| Kytamer ® PC | 0.05 |
| PET ® 75 lanolin | 1.0 |
| U-Con ® fluid AP | 1.0 |
| Water | 37.44 |
| Fragrance 1626-HR | 0.01 |
| Sodium Hydroxide (5N) | q.s. |
| Hydrochloric Acid (6N) | q.s. |

Kytamer ® was mixed with water until the solid was completely dissolved and a clear solution was obtained. Ethanol, parachlorometaxylenol, PEG ® 75 lanolin, U-Con ® fluid AP and the fragrance were then mixed into the clear solution. The pH of the solution was then adjusted to about 5.0±0.5 by the addition of sodium hydroxide and hydrochloric acid.

Paper substrates were then dipped into antimicrobial formulation B and dried.

EXAMPLE 3

Preparation of Antimicrobial Formulation C and Application To A Paper Substrate

Antimicrobial formulation C was formed with the following ingredients:

| Ingredients | Weight Percent |
| --- | --- |
| Isopropanol | 70.0 |
| Chlorhexidine Gluconate (20% w/v) | 1.0 |
| polyvinyl pyrrolidone-polyvinyl acetate (PVP-PVA) | 0.5 |
| PET ® 75 lanolin | 1.0 |
| U-Con ® fluid AP | 1.0 |
| Water | 26.49 |
| Fragrance 1626-HR | 0.01 |
| Sodium Hydroxide (5N) | q.s. |
| Hydrochloric Acid (6N) | q.s. |

PVP-PVA was mixed with water until the solid was completely dissolved and a clear solution was obtained. Isopropanol, chlorhexidine gluconate, PEG ® 75 lanolin, U-Con ® fluid AP and the fragrance were then mixed into the clear solution. The pH of the solution was then adjusted to about 5.0±0.5 by the addition of sodium hydroxide and hydrochloric acid.

Paper substrates were then dipped into formulation antimicrobial C and dried.

EXAMPLE 4

Evaluation of Dry Antimicrobial Towels Samples

Dry antimicrobial towel samples were prepared in accordance with Example 1 above and evaluated by panel of male and female subjects. Each subject dried their hands with a towel after washing with liquid soap, chlorhexidine gluconate scrub solution and iodophor scrub solution. In all cases, the subjects reported that their hands were smoother feeling, with no redness and dryness and without an itchy feeling after drying with the towel.

Then the subjects washed their hands in 500 mls of deionized water. The deionized water was then analyzed in UV/VIS spectrophotometer. The presence of chlorhexidine gluconate was detected.

The evaluation conducted for tiffs example shows that the antimicrobial agent in the dry towel transfers on to the skin along with the emollient and that the presence of the transferred antimicrobial agent on the skin benefits in prolonging the antimicrobial effectiveness of the scrubbed and prepped skin.

EXAMPLE 5

Evaluation of Dry Antimicrobial Towel Samples

Dry antimicrobial towel samples were prepared in accordance with Example 1 and placed on a nutrient agar plate. The towel samples were then challenged with a microbial culture and incubated at 30° C.–35° C. on a nutrient agar plate for a minimum of 48 hours. Each towel sample was then evaluated for growth and the results reported in Table 1. A control sample was also tested by performing the above procedure using a sterile non-treated towel.

TABLE 1

| Towel Sample | Microbial Culture | Growth |
| --- | --- | --- |
| A (control) | *Staphylococcus aureus* | Positive |
| B | *Staphylococcus aureus* | Negative |

TABLE 1-continued

| Towel Sample | Microbial Culture | Growth |
| --- | --- | --- |
| C | Pseudomonas aeruginosa | Negative |
| D | Escherichia coli | Negative |
| E | Candida albicans | Negative |

The evaluation conducted for this example shows that the dry antimicrobial towel of the present invention inhibits microbial growth.

What is claimed is:

1. A dry wipe comprising an absorbent paper substrate which is coated and dried with an antimicrobial formulation comprising:
   (a) isopropanol or ethanol in an amount from about 50 to about 75 weight percent of the total composition;
   (b) chlorhexidine gluconate or parachlorometaylenol in an amount from about 0.05 to about 1.5 weight percent of the total composition;
   (c) chitosan in an amount from about 0.01 to about 2.5 weight percent of the total composition;
   (d) a polyalkylene glycol in an amount from about 0.5 to about 1.5 weight percent of the total composition.
   (e) a moisturizer and/or emollient in an amount from about 0.5 to about 1.5 weight percent of the total composition;
   (f) water in an amount from about 24 to about 27 weight percent of the total composition; and
   (g) a suitable pH adjusting component.

2. The dry wipe of claim 1 wherein said antimicrobial formulation has a pH from about 4.5 to about 7.5.

* * * * *